United States Patent
Boutin et al.

(10) Patent No.: US 11,259,875 B2
(45) Date of Patent: *Mar. 1, 2022

(54) PROXIMITY-TRIGGERED COMPUTER-ASSISTED SURGERY SYSTEM AND METHOD

(71) Applicant: ORTHOSOFT ULC, Montreal (CA)

(72) Inventors: Yannick Boutin, Montreal (CA); Jean-Guillaume Abiven, Montreal (CA); Mathieu Chevrier, Roxboro (CA)

(73) Assignee: ORTHOSOFT ULC, Montreal (CA)

( * ) Notice: Subject to any disclaimer, the term of this patent is extended or adjusted under 35 U.S.C. 154(b) by 240 days.

This patent is subject to a terminal disclaimer.

(21) Appl. No.: 15/705,953

(22) Filed: Sep. 15, 2017

(65) Prior Publication Data
US 2018/0125580 A1 May 10, 2018

Related U.S. Application Data

(60) Continuation of application No. 14/188,036, filed on Feb. 24, 2014, now Pat. No. 9,788,904, which is a (Continued)

(51) Int. Cl.
*A61B 34/00* (2016.01)
*A61B 34/20* (2016.01)
(Continued)

(52) U.S. Cl.
CPC .............. *A61B 34/20* (2016.02); *A61B 34/10* (2016.02); *A61B 34/30* (2016.02); *G16H 20/40* (2018.01);
(Continued)

(58) Field of Classification Search
CPC ..................... A61B 34/20; A61B 2034/2051
See application file for complete search history.

(56) References Cited

U.S. PATENT DOCUMENTS 5,682,886 A * 11/1997 Delp .................... A61B 17/154
128/920
6,434,507 B1  8/2002 Clayton et al.
(Continued)

FOREIGN PATENT DOCUMENTS

WO    2009063421 A1    5/2009

*Primary Examiner* — Nicholas W Woodall
(74) *Attorney, Agent, or Firm* — Norton Rose Fulbright Canada LLP

(57) ABSTRACT

A computer-assisted surgery system comprises a first surgical device with a tracking unit tracked during a surgical procedure and adapted to perform a first function associated to the surgical procedure. A second surgical device is adapted to perform a second function associated to the surgical procedure. A triggered unit is triggered when the first surgical device and the second surgical device reach a predetermined proximity relation. A surgical procedure processing unit tracks the first surgical device. A trigger detector detects a triggering of the triggered unit. A CAS application operates steps of a surgical procedure. A controller commands the CAS application to activate a selected step associated with the second function in the surgical procedure when the trigger detector signals a detection. An interface displays information about the selected step in the surgical procedure.

14 Claims, 4 Drawing Sheets

Related U.S. Application Data division of application No. 12/872,415, filed on Aug. 31, 2010, now Pat. No. 8,696,675.

(51) Int. Cl.
  *A61B 34/30* (2016.01)
  *G16H 40/67* (2018.01)
  *A61B 34/10* (2016.01)
  *G16H 20/40* (2018.01)

(52) U.S. Cl.
  CPC ...... *G16H 40/67* (2018.01); *A61B 2034/2048* (2016.02); *A61B 2034/254* (2016.02)

(56) References Cited

U.S. PATENT DOCUMENTS

| | | | |
|---|---|---|---|
| 6,946,956 B2 | 9/2005 | Hayashi et al. | |
| 6,954,148 B2 | 10/2005 | Pulkkinen et al. | |
| 8,265,790 B2 * | 9/2012 | Amiot | G01C 21/16 700/245 |
| 2003/0078494 A1 | 4/2003 | Panescu et al. | |
| 2004/0243148 A1 * | 12/2004 | Wasielewski | A61B 17/00 606/130 |
| 2005/0143676 A1 * | 6/2005 | De Guise | A61B 5/103 600/595 |
| 2006/0015120 A1 * | 1/2006 | Richard | A61B 90/06 606/102 |
| 2006/0122491 A1 * | 6/2006 | Murray | A61B 17/157 600/414 |
| 2006/0155291 A1 | 7/2006 | Farrar et al. | |
| 2006/0200025 A1 * | 9/2006 | Elliott | A61B 90/36 600/424 |
| 2007/0225731 A1 | 9/2007 | Couture et al. | |
| 2007/0270680 A1 | 11/2007 | Sheffer et al. | |
| 2009/0099570 A1 | 4/2009 | Paradis et al. | |
| 2009/0240169 A1 | 9/2009 | Warkentine et al. | |
| 2009/0248044 A1 | 10/2009 | Amiot et al. | |
| 2010/0063508 A1 | 3/2010 | Borja et al. | |
| 2010/0249796 A1 | 9/2010 | Nycz | |
| 2011/0257653 A1 | 10/2011 | Hughes | |
| 2011/0275957 A1 | 11/2011 | Bhandari | |

* cited by examiner

PROXIMITY-TRIGGERED COMPUTER-ASSISTED SURGERY SYSTEM AND METHOD

CROSS-REFERENCE TO RELATED APPLICATION

The present application is a continuation of U.S. patent application Ser. No. 14/188,036 filed on Feb. 24, 2014 which is a divisional application of U.S. patent application Ser. No. 12/872,415 filed on Aug. 31, 2010, incorporated herewith by reference.

FIELD OF THE APPLICATION

The present application relates to computer-assisted surgery, and more particularly to surgical tools used in computer-assisted surgery and triggering associated therewith.

BACKGROUND OF THE ART

Computer-assisted surgery has evolved over the years to use the computational speed of computers to guide surgeons and operating-room personnel in performing orthopedic procedures on the bones with high degrees of precision and accuracy. In order to lessen the requirements of hardware in the operating room, microelectromechanical systems (MEMS) such as gyroscopes and accelerometers are used in calculating orientation and/or position of surgical tools and bones.

MEMS are used in addition or as an alternative to other types of trackers, such as optical tracking systems (e.g., Navitrack™). In some cases, optical tracking systems can be replaced with MEMS, therefore removing bulky optical tracker devices on tools and bones. Because of the minute format of MEMS, it is even contemplated to perform computer-assisted surgery without a self-standing monitor, by instead providing all information within the surgical field with LED indicators or screens on tools. It is desirable to automate computer-assisted surgery using MEMS to accelerate surgical procedures.

SUMMARY OF THE APPLICATION

Therefore, in accordance with the present application, there is provided a computer-assisted surgery system comprising: a first surgical device with a tracking unit tracked during a surgical procedure and adapted to perform a first function associated to the surgical procedure; a second surgical device adapted to perform a second function associated to the surgical procedure; a triggered unit triggered when the first surgical device and the second surgical device reach a predetermined proximity relation; a surgical procedure processing unit tracking at least the first surgical device, the surgical procedure processor comprising a trigger detector detecting a triggering of the triggered unit, a computer-assisted surgery application operating steps of a surgical procedure, a controller for commanding the computer-assisted surgery application to activate a selected step associated with the second function in the surgical procedure when the trigger detector signals a detection, and an interface for displaying information about the selected step in the surgical procedure.

Further in accordance with the present application, there is provided a method for progressing through steps of a surgical procedure of a computer-assisted surgery application, comprising: tracking at least a first surgical device adapted to perform a first function associated with the surgical procedure; detecting a predetermined proximity relation between the first surgical device and a second surgical device adapted to perform a second function associated with the surgical procedure; activating a selected step of the surgical procedure associated with the second function when the predetermined proximity relation is detected; and displaying information related to the selected step.

DESCRIPTION OF THE EXEMPLARY EMBODIMENTS

Figure 1:
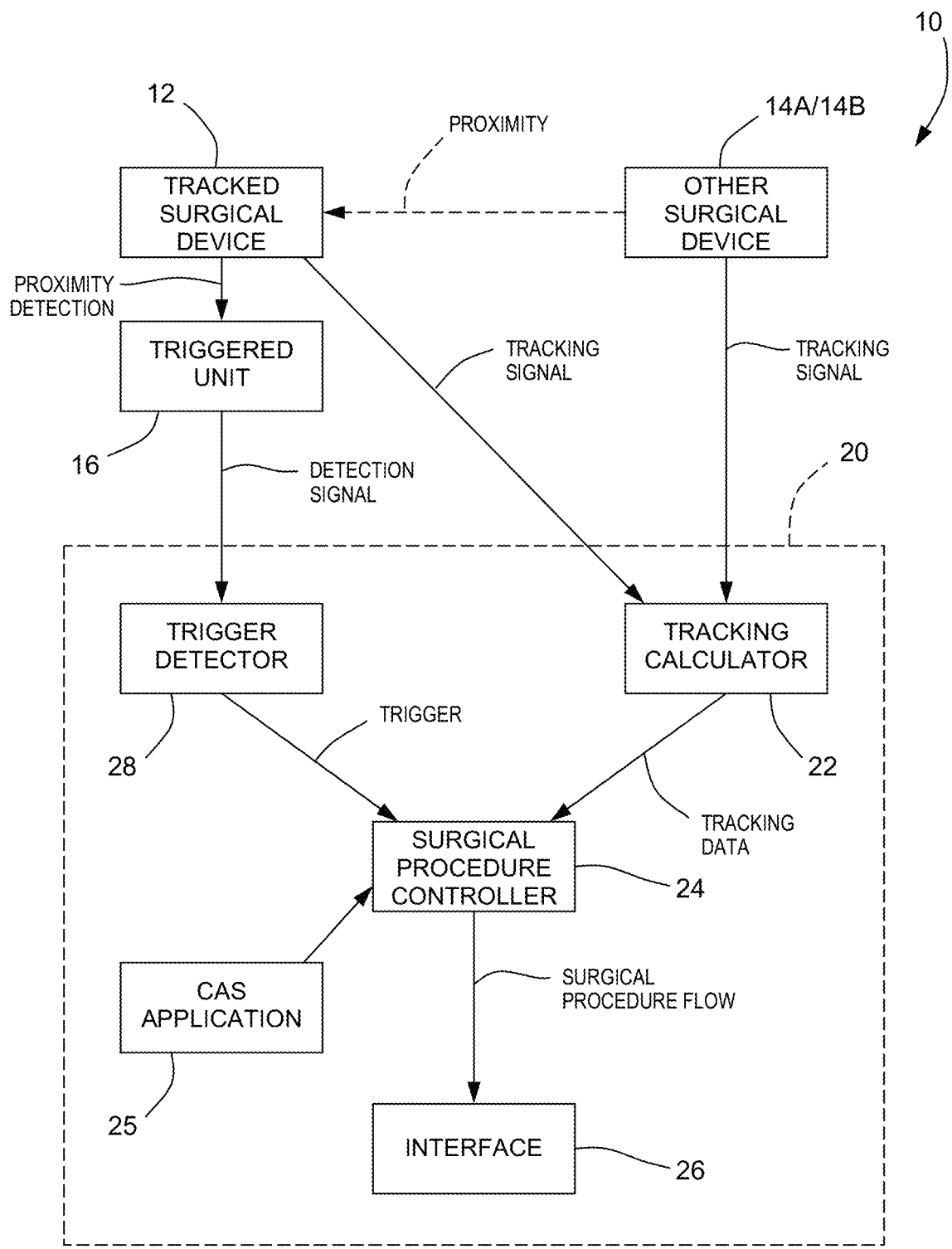
FIG. 1 is a block diagram of a proximity-triggered computer-assisted surgery system in accordance with an exemplary embodiment of the present application.

Referring to the drawings, and more particularly to FIGS. 2, 3, 4A and 4B, there is illustrated a lower leg of a patient, with soft tissue removed so as to expose an upper end of the tibia A, for use with a proximity-triggered computer-assisted surgery system of the exemplary embodiment. Although the computer-assisted surgery system and associated method are described and illustrated as used for tibial alterations during knee-replacement surgery, it is understood that the proximity-triggered computer-assisted surgery system and method of the present embodiment may be used in all other types of orthopedic surgery, such as total knee replacement, total hip replacement, spine surgery, or any other type of orthopedic surgery requiring surgical devices as described for the exemplary embodiment.

Referring to FIG. 1, the proximity-triggered computer-assisted surgery (CAS) system is generally shown at 10. The CAS system 10 may feature a plurality of surgical devices. In the illustrated embodiment, the CAS system 10 has a tracked surgical device 12 that is secured to a bone. In the exemplary embodiment of FIG. 1, the tracked surgical device 12 is a MEMS-operated reference unit that is secured to the bone so as to provide tracking data (i.e., orientation and/or position information) related to the bone A through various calibration and referencing steps.

Figure 2:
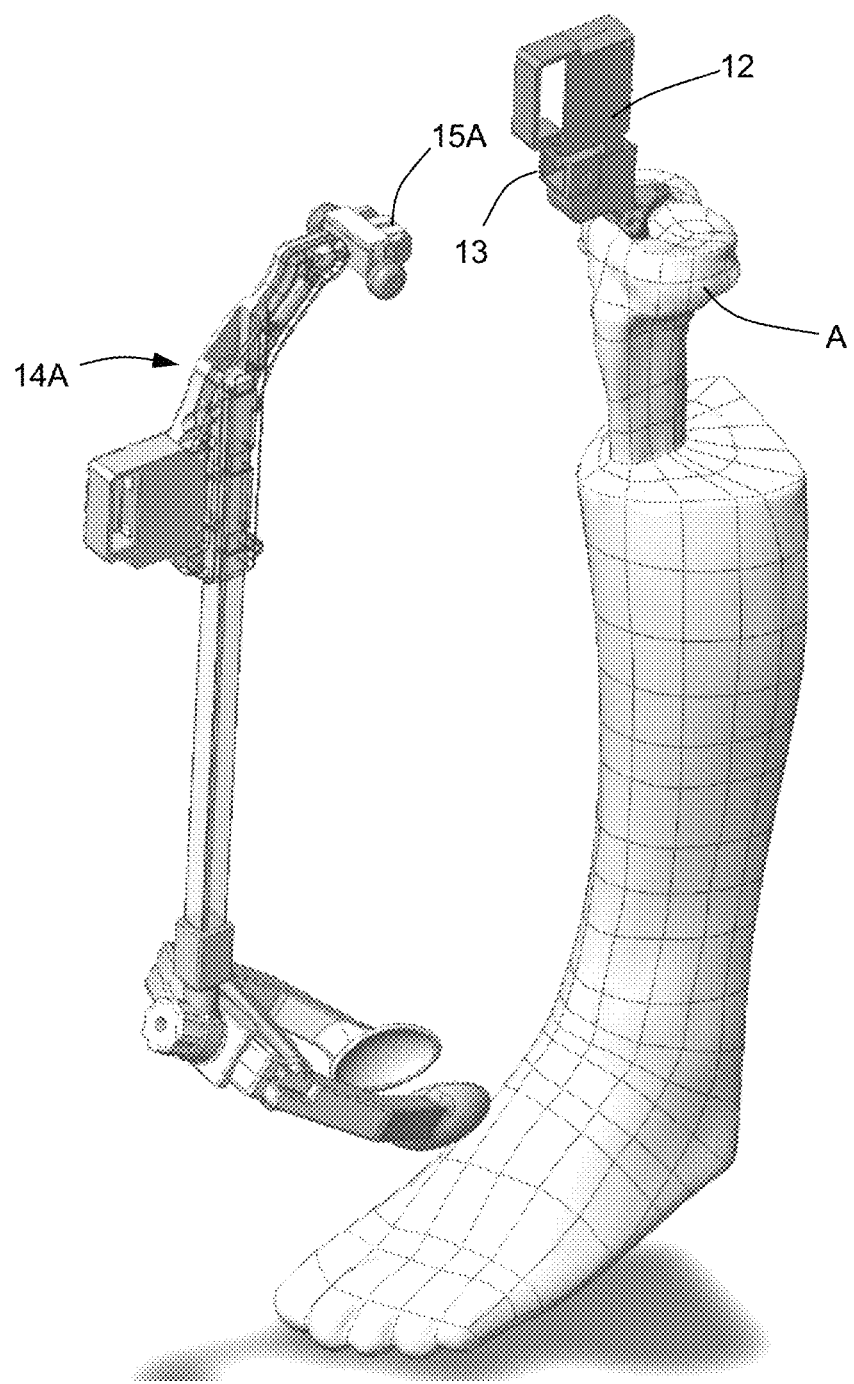
FIG. 2 is a schematic view of mating surgical devices with respect to a bone, as used with the computer-assisted surgery system of FIG. 1.
Figure 3:
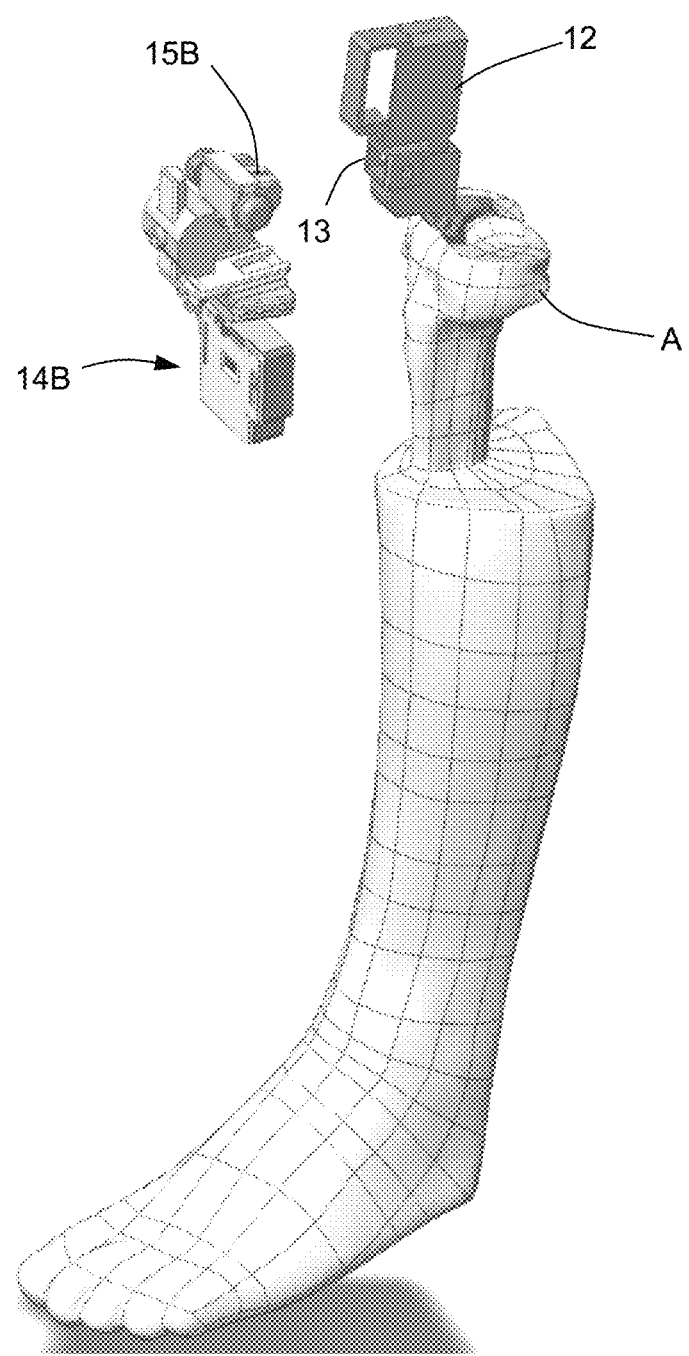
FIG. 3 is a schematic view of mating surgical devices with respect to a bone, as used with the computer-assisted surgery system of FIG. 1.

As shown in FIGS. 2 and 3, the tracked surgical device 12 is a tibial reference secured to an upper end of the tibia A, so as to act as a tracking reference. The tibial reference 12 has a female connector 13 in order to receive other surgical devices therein. In one embodiment, other surgical devices in mating engagement with the tracked surgical device 12 will also be tracked by the geometrical relation between the tracked surgical device 12 and the other surgical device. In FIG. 2, the other surgical device is illustrated at 14A and is known as a tibial digitizer. In FIG. 3, the other surgical device 14B is a cutting block. The tibial digitizer and the cutting block respectively have male connectors 15A and 15B.

In the exemplary embodiment, the tracked surgical device 12 has electronic circuitry, as it operates MEMS to provide the tracking data. A triggered unit 16 (FIG. 1) is provided on the tracked surgical device 12, for instance as part of the electronic circuitry, so as to be triggered when a mating engagement is completed between the female connector 13 of the tracked surgical device 12 and the male connector 15 of the other surgical device 14. The triggered unit 16 may be any one of a plurality of units. For instance, the triggered unit 16 may be a simple switch that is provided in the female connector 13 so as to be triggered by the contact with the male connector 15. Other alternatives include a magnet and appropriate sensor, respectively in opposite devices, proximity switches and sensors, a conductive element and an open circuit in opposite devices, or any other appropriate type of triggered unit or switch.

The proximity-triggered CAS system 10 features a proximity-triggered CAS processing unit 20 that comprises a tracking calculator 22 in order to track the surgical device and the surgical devices 14A/14B through the connected relation with the surgical device 12, or independently therefrom of the surgical device 14A/14B have their own MEMS. The tracking calculator 22 receives tracking signals from the MEMS of the surgical devices and converts the data with prior calibration and referencing information into tracking values related to the surgical devices 12, 14A and/or 14B, as well as related to the bone A or any other appropriate bone that has been calibrated and referenced as well.

A surgical procedure controller 24 operates a CAS application 25 that guides the surgeon and personnel of the operating room in following a series of manual steps according to the CAS application to define bone axes, tool axes, models, as well as in providing surgical step information, to guide surgical operations on the bones. The CAS application 25 follows a specific flow of steps according to the information entered by the operator of the CAS system 10, as well as through the tracking data provided by the tracking calculator 22. The resulting information is displayed on an interface 26, typically a monitor of a self-standing station, or screen or LED indicators directly on the surgical devices.

A trigger detector 28 is provided in the CAS processing unit 20 so as to receive a detection signal from the triggered unit 16. Upon receiving the detection signal, the trigger detector 28 signals the triggering to the surgical procedure controller 24. The trigger detector 28 may perform a confirmation step, for instance by confirming that the surgical device 14 is sufficiently close to the surgical device 12, when proximity sensors are used. Moreover, if the devices 12 and 14 matingly engage, the trigger detector 28 may require a sustained detection signal to confirm the triggering. These confirmation steps may be performed by the triggered unit 16 as well, in both case by the presence of a conditions database.

The triggering is automatic further to the positioning of the surgical device 14 in proximity to or in contact with the surgical device 12. Accordingly, the surgical procedure controller 24 will alter its flow of operations following the receipt of a signal from the trigger detector 28 to further advance the flow of steps of the surgical procedure, as observed on the interface 26, for instance by the change of data on the screen. Accordingly, by performing this action, one step of interfacing between the operator and the CAS system 10 is removed, and replaced by an intuitive step required in most standard surgical techniques for a given type of procedure.

Figure 4A:
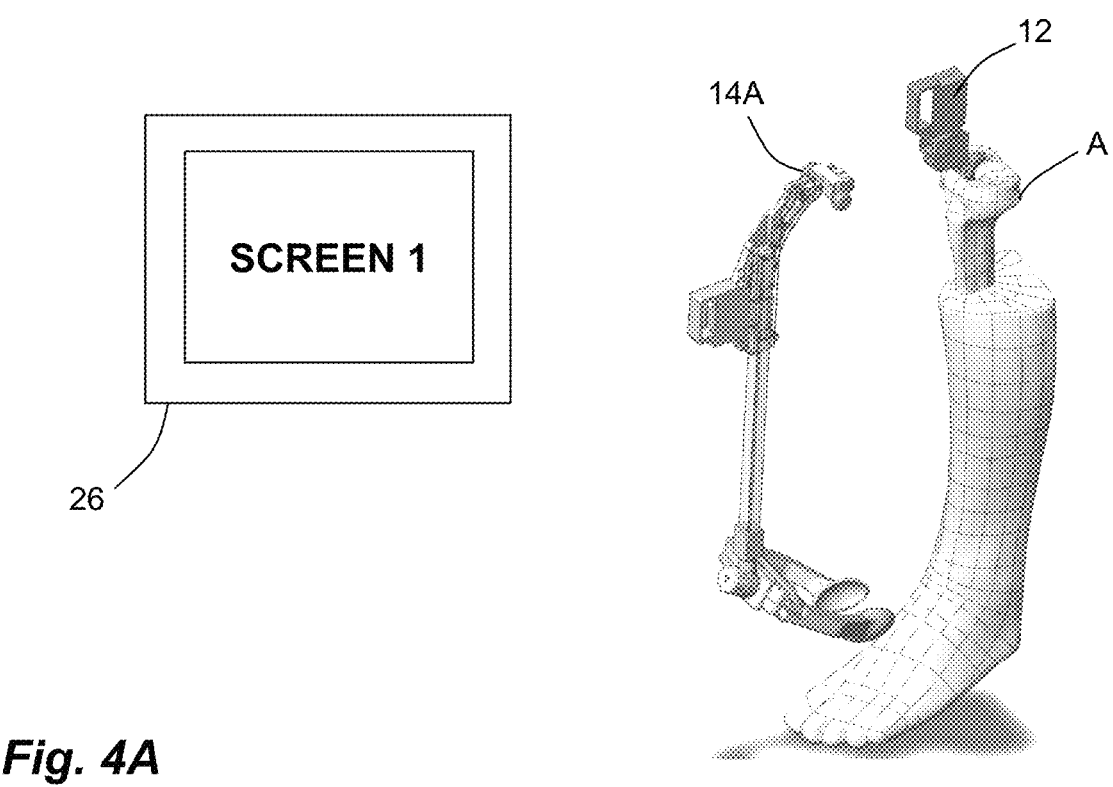
FIG. 4A is a schematic view of the mating surgical devices of FIG. 2 with a CAS monitor, prior to mating.
Figure 4B:
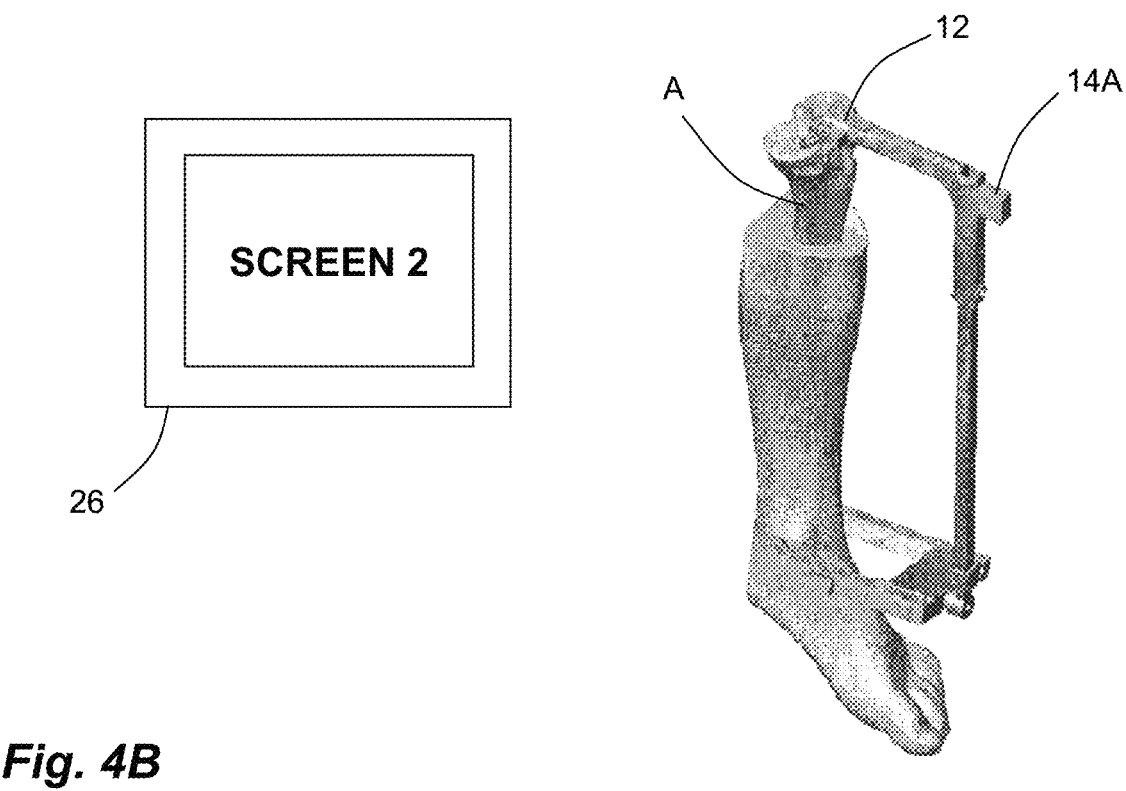
FIG. 4B is a schematic view of the mating surgical devices of FIG. 2 with the CAS monitor, after mating.

Referring to FIGS. 4A and 4B, there is illustrated the method of automatically triggering the CAS system by proximity. In FIG. 4A, the tibial reference 12 is secured to the tibia A, and is calibrated and referenced. Accordingly, the tibia A is tracked for subsequent surgical steps thereon.

The interface 26 shows screen 1, in accordance with the progress that is made in the surgical procedure. Screen 1 may therefore display tracking information (e.g., axes, bone models, values) pertaining to the bone A from the tracking of the tibial reference 12. Moreover, according to the surgical procedure, screen 1 indicates that the next step is to connect the tibial digitizer 14A to the tibial reference 12, by way of the mating connection (e.g., FIG. 2) therebetween.

As mentioned previously, the positioning of the surgical device 14 may not require the physical interconnection with the surgical device 12. The data on the screen 1 may pertain to the installation of the surgical device 14 at a specific location on the bone A, per surgical technique, for instance at a given distance from the surgical device 12 as detectable by proximity switches and sensors.

Referring to FIG. 4B, the tibial digitizer 14A is matingly connected to the tibial reference 12, resulting in the trigger of the triggered unit 16. Accordingly, if the triggering conditions are met (e.g., time lapsed, proximity, etc.), the CAS processing unit 20 automatically changes the data on the interface 26, as indicated by screen 2 in FIG. 4B. The change of data may be the automatic change of mode in the procedure flow to start gathering data associated with the tibial digitizer 14A (e.g., the registration of a tibial axis), going from a commanding mode to a data-collecting mode. The change of data may also be an indication that the devices 12 and 14 are adequately connected to one another, thereby prompting the operator of the CAS system 10 to perform another step.

The aforementioned steps are part of a complete set of steps, some being mandatory or optional or prerequisites as defined in the surgical technique, operated by the CAS processing unit 20 in accordance with the CAS application 25. The aforementioned steps may be repeated during the surgical procedure. For instance, when installing the cutting block 14B (FIG. 3), the automatic trigger may also cause a change in the surgical procedure flow.

The invention claimed is:

1. A method for progressing through steps of a surgical procedure of a computer-assisted surgery application, comprising:
    establishing, in a processor, a predetermined proximity relation between at least a first surgical device adapted to perform a first function associated with the surgical procedure, and a second surgical device adapted to perform a second function associated with the surgical procedure, wherein the predetermined proximity relation is associated with a selected step of the surgical procedure associated with the second function;
    tracking at least the first surgical device;
    detecting the predetermined proximity relation between the first surgical device and the second surgical device adapted to perform the second function associated with the surgical procedure, as the first surgical device is brought in said predetermined proximity relation while the first surgical device is tracked;
    as an automatic response to the predetermined proximity relation being detected, automatically triggering an activation of the selected step of the surgical procedure associated with the second function; and
    displaying information related to the selected step.

2. The method according to claim 1, further wherein tracking the first surgical device comprises receiving tracking data from a micro-electromechanical system.

3. The method according to claim 1, wherein detecting the predetermined proximity relation comprises detecting a mating engagement between the first surgical device and the second surgical device.

4. The method according to claim 3, further comprising tracking the second surgical device.

5. The method according to claim 4, wherein tracking the second surgical device comprises tracking the second surgical device from the tracking of the first surgical device and from a known geometry of the mating engagement between the surgical devices.

6. The method according to claim 4, wherein displaying information related to the selected step comprises displaying information related to the tracking of the second surgical device.

7. The method according to claim 1, further comprising confirming that the detected predetermined proximity relation respects predetermined conditions prior to automatically triggering the action of the selected step.

8. The method according to claim 1, wherein tracking the first surgical device comprises tracking a tibial reference on a tibia of a patient.

9. The method according to claim 8, further comprising tracking the second surgical device with the second surgical device being a tibial digitizer, and wherein displaying information related to the selected step comprises displaying a tibial axis.

10. The method according to claim 1, wherein tracking the first surgical device is part of a given step of the surgical procedure.

11. The method according to claim 10, wherein automatically triggering the activation of the selected step includes changing from the given step to the selected step in the surgical procedure of a computer-assisted surgery application.

12. The method according to claim 10, wherein tracking the first surgical device includes displaying information relating to the given step associated with the first function.

13. The method according to claim 12, wherein automatically triggering the activation of the selected step includes causing a change in the displaying of information.

14. The method according to claim 1, wherein detecting a predetermined proximity relation includes receiving a signal from a proximity switch associated with at least one of the first surgical device and the second surgical device.

* * * * *